US008923942B2

(12) United States Patent
Bernreuter (10) Patent No.: US 8,923,942 B2
(45) Date of Patent: Dec. 30, 2014

(54) IN VIVO BLOOD SPECTROMETRY (76) Inventor: Peter Bernreuter, Dettingen (DE)

( * ) Notice: Subject to any disclaimer, the term of this patent is extended or adjusted under 35 U.S.C. 154(b) by 605 days.

(21) Appl. No.: 12/946,506

(22) Filed: Nov. 15, 2010

(65) Prior Publication Data

US 2011/0060200 A1 Mar. 10, 2011

Related U.S. Application Data

(63) Continuation of application No. 11/078,399, filed on Mar. 14, 2005, now Pat. No. 7,865,223.

(51) Int. Cl.
*A61B 5/1455* (2006.01)
*A61B 5/1464* (2006.01)
*A61B 5/00* (2006.01)

(52) U.S. Cl.
CPC ........... *A61B 5/1464* (2013.01); *A61B 5/14553* (2013.01); *A61B 5/14552* (2013.01); *A61B 5/6838* (2013.01); *A61B 5/6826* (2013.01); *A61B 2562/0242* (2013.01); *A61B 5/14551* (2013.01)
USPC ........................................................ 600/323

(58) Field of Classification Search
USPC .................................. 600/310, 322, 323, 336
See application file for complete search history.

(56) References Cited

U.S. PATENT DOCUMENTS

| | | |
|---|---|---|
| 2,706,927 A | 4/1955 | Wood |
| 2,790,438 A | 4/1957 | Taplin et al. |
| 3,412,729 A | 11/1968 | Smith, Jr. |
| 3,068,742 A | 8/1969 | Hicks, Jr. et al. |
| 3,461,856 A | 8/1969 | Polyani |
| 3,638,640 A | 2/1972 | Shaw |
| 3,704,706 A | 12/1972 | Herczfeld et al. |
| 3,709,612 A | 1/1973 | Clemens |
| 3,866,599 A | 2/1975 | Johnson |
| 3,998,550 A | 12/1976 | Konishi et al. |
| 4,014,321 A | 3/1977 | March |
| 4,029,085 A | 6/1977 | DeWitt et al. |
| 4,086,915 A | 5/1978 | Kofsky et al. |
| 4,119,406 A | 10/1978 | Ciemens |
| 4,129,125 A | 12/1978 | Lester et al. |
| 4,167,331 A | 9/1979 | Nielsen |
| 4,222,389 A | 9/1980 | Rubens |

(Continued)

FOREIGN PATENT DOCUMENTS

JP 05212016 A 8/1993
JP 630915 A 2/1994

(Continued)

OTHER PUBLICATIONS

U.S. Appl. No. 12/618,120, Restriction Requirement mailed Jul. 26, 2012, 12 pgs.

(Continued)

*Primary Examiner* — Eric Winakur
(74) *Attorney, Agent, or Firm* — Schwegman Lundberg & Woessner, P.A.

(57) ABSTRACT

A process and apparatus for determining the arterial and venous oxygenation of blood in vivo with improved precision. The optical properties of tissue are measured by determination of differential and total attenuations of light at a set of wavelengths. By choosing distinct wavelengths and using the measured attenuations, the influence of variables such as light scattering, absorption and other optical tissue properties is canceled out or minimized.

33 Claims, 10 Drawing Sheets

(56) References Cited

U.S. PATENT DOCUMENTS

| | | |
|---|---|---|
| 4,223,680 A | 9/1980 | Jobsis |
| 4,224,948 A | 9/1980 | Cramer et al. |
| 4,259,963 A | 4/1981 | Huch |
| 4,266,554 A | 5/1981 | Hamaguri |
| 4,281,645 A | 8/1981 | Jobsis |
| 4,321,930 A | 3/1982 | Jobsis et al. |
| 4,380,240 A | 4/1983 | Jobsis et al. |
| 4,416,285 A | 11/1983 | Shaw et al. |
| 4,447,884 A | 5/1984 | Wade |
| 4,452,250 A | 6/1984 | Chance et al. |
| 4,469,107 A | 9/1984 | Asmar et al. |
| 4,510,938 A | 4/1985 | Jobsis et al. |
| 4,576,173 A | 3/1986 | Parker et al. |
| 4,648,892 A | 3/1987 | Kittrell et al. |
| 4,655,225 A | 4/1987 | Dahne et al. |
| 4,700,708 A | 10/1987 | New, Jr. et al. |
| 4,714,341 A | 12/1987 | Hamaguri et al. |
| 4,738,267 A | 4/1988 | Lazorthes et al. |
| 4,773,422 A | 9/1988 | Isaacson et al. |
| 4,774,679 A | 9/1988 | Carlin |
| 4,800,495 A | 1/1989 | Smith |
| 4,800,885 A | 1/1989 | Johnson |
| 4,805,623 A | 2/1989 | Jobsis |
| 4,824,242 A | 4/1989 | Frick et al. |
| 4,836,207 A | 6/1989 | Bursell et al. |
| 4,840,485 A | 6/1989 | Gratton |
| 4,846,183 A | 7/1989 | Martin |
| 4,869,254 A | 9/1989 | Stone et al. |
| 4,880,304 A | 11/1989 | Jaeb et al. |
| 4,908,762 A | 3/1990 | Suzuki et al. |
| 4,926,867 A | 5/1990 | Kanda et al. |
| 4,942,877 A | 7/1990 | Sakai et al. |
| 4,972,331 A | 11/1990 | Chance |
| 5,032,024 A | 7/1991 | Cope |
| 5,035,243 A | 7/1991 | Muz |
| 5,057,695 A | 10/1991 | Hirao et al. |
| 5,062,431 A | 11/1991 | Potter |
| 5,074,306 A | 12/1991 | Green |
| 5,088,493 A | 2/1992 | Giannini et al. |
| 5,090,415 A | 2/1992 | Yamashita et al. |
| 5,119,815 A | 6/1992 | Chance |
| 5,137,355 A | 8/1992 | Barbour et al. |
| 5,139,025 A | 8/1992 | Lewis et al. |
| 5,140,989 A | 8/1992 | Lewis et al. |
| 5,198,977 A | 3/1993 | Salb |
| 5,213,105 A | 5/1993 | Gratton et al. |
| 5,217,013 A | 6/1993 | Lewis et al. |
| 5,218,962 A | 6/1993 | Mannheimer et al. |
| 5,222,495 A | 6/1993 | Clarke et al. |
| 5,253,646 A | 10/1993 | Delpy et al. |
| 5,261,410 A | 11/1993 | Alfano et al. |
| 5,266,554 A | 11/1993 | Suchy et al. |
| 5,277,181 A | 1/1994 | Mendelson et al. |
| 5,285,783 A | 2/1994 | Secker |
| 5,318,023 A | 6/1994 | Vari et al. |
| 5,349,961 A | 9/1994 | Stoddart et al. |
| 5,385,143 A | 1/1995 | Aoyagi |
| 5,431,170 A * | 7/1995 | Mathews ............... 600/323 |
| 5,465,714 A | 11/1995 | Scheuing |
| 5,477,853 A | 12/1995 | Farkas |
| 5,482,031 A | 1/1996 | Lambert |
| 5,482,034 A | 1/1996 | Lewis |
| 5,490,523 A | 2/1996 | Isaacson et al. |
| 5,497,769 A | 3/1996 | Gratton et al. |
| 5,524,617 A | 6/1996 | Mannheimer |
| 5,529,064 A | 6/1996 | Rall |
| 5,551,422 A | 9/1996 | Simonsen et al. |
| 5,551,423 A | 9/1996 | Sugiura |
| 5,584,269 A | 12/1996 | MacKenzie |
| 5,697,367 A | 12/1997 | Lewis et al. |
| 5,720,284 A * | 2/1998 | Aoyagi et al. ............ 600/322 |
| 5,772,589 A | 6/1998 | Bernreuter |
| 5,779,631 A | 7/1998 | Chance |
| 5,792,052 A | 8/1998 | Isaacson |
| 5,795,292 A | 8/1998 | Lewis et al. |
| 5,800,349 A | 9/1998 | Isaacson et al. |
| 5,873,821 A | 2/1999 | Chance et al. |
| 5,879,294 A | 3/1999 | Anderson |
| 5,902,235 A | 5/1999 | Lewis et al. |
| 5,922,607 A | 7/1999 | Bernreuter |
| 6,226,540 B1 | 5/2001 | Bernreuter |
| 6,285,895 B1 | 9/2001 | Ristolainen et al. |
| 6,549,795 B1 | 4/2003 | Chance |
| 6,597,931 B1 | 7/2003 | Cheng et al. |
| 6,615,065 B1 | 9/2003 | Barrett et al. |
| 6,985,763 B2 | 1/2006 | Boas et al. |
| 7,047,054 B2 | 5/2006 | Benni |
| 7,072,701 B2 | 7/2006 | Chen et al. |
| 7,865,223 B1 | 1/2011 | Bernreuter |
| 8,055,321 B2 | 11/2011 | Bernreuter |
| 8,725,226 B2 | 5/2014 | Isaacson |
| 2002/0058865 A1 | 5/2002 | Cheng |
| 2002/0082488 A1 | 6/2002 | Al-Ali et al. |
| 2002/0161290 A1 | 10/2002 | Chance |
| 2002/0198443 A1 | 12/2002 | Ting |
| 2003/0181798 A1 | 9/2003 | Al-Ali |
| 2004/0024297 A1 | 2/2004 | Chen et al. |
| 2005/0075549 A1 | 4/2005 | Kondoh |
| 2005/0228291 A1 | 10/2005 | Chance |
| 2006/0189862 A1 | 8/2006 | Casciani et al. |
| 2007/0055119 A1 | 3/2007 | Lash et al. |
| 2008/0015424 A1 | 1/2008 | Bernreuter |
| 2008/0058638 A1 | 3/2008 | Zhu et al. |
| 2008/0208011 A1 | 8/2008 | Shuler |
| 2009/0247853 A1 | 10/2009 | Debreczeny |
| 2009/0281403 A1 | 11/2009 | Benni |
| 2010/0094134 A1 | 4/2010 | Zhu et al. |
| 2012/0184830 A1 | 7/2012 | Balberg et al. |
| 2012/0190946 A1 | 7/2012 | Bernreuter |

FOREIGN PATENT DOCUMENTS

| | | |
|---|---|---|
| JP | 630916 A | 2/1994 |
| JP | 08-271600 A | 10/1996 |
| JP | 11244268 A | 9/1999 |
| JP | 2004290412 A | 10/2004 |
| JP | 2005533609 A | 11/2005 |
| JP | 2005535359 A | 11/2005 |
| JP | 2008532680 A | 8/2008 |
| JP | 2010534083 A | 11/2010 |
| WO | WO-0181798 A1 | 11/2001 |
| WO | WO-2004010844 A2 | 2/2004 |
| WO | WO-2006094279 A1 | 9/2006 |
| WO | WO-2006124696 A1 | 11/2006 |
| WO | WO-2007012931 A2 | 2/2007 |
| WO | WO-2009013608 A2 | 1/2009 |
| WO | WO-2009013608 A3 | 1/2009 |
| WO | WO-2010056973 A1 | 5/2010 |

OTHER PUBLICATIONS

U.S. Appl. No. 13/283,044, Preliminary Amendment filed Apr. 10, 2012, 6 pgs.

European Application Serial No. 06795079.0, Response filed May 16, 2012 to Office Action mailed Mar. 20, 2012, 12 pgs.

Japanese Application Serial No. 2008-501451, Response filed Apr. 20, 2012 to Office Action mailed Oct. 21, 2011, 22 pgs.

U.S. Appl. No. 11/780,997, Examiner Interview Summary mailed May 26, 2011, 4 pgs.

U.S. Appl. No. 11/780,997, Notice of Allowance mailed Jul. 12, 2011, 7 pgs.

European Application No. 06795079.0, Office Action mailed Aug. 1, 2011, 6 pgs.

Japanese Application Serial No. 2008-501451, Notice of Reason for Rejection mailed Oct. 21, 2011, 8 pgs.

U.S. Appl. No. 11/078,399, Examiner Interview Summary mailed Jun. 10, 2010, 3 pgs.

U.S. Appl. No. 11/078,399, Final Office Action mailed Jun. 10, 2010, 12 pgs.

U.S. Appl. No. 11/078,399, Non-Final Office Action mailed Dec. 3, 2009, 23 pgs.

U.S. Appl. No. 11/078,399, Notice of Allowance mailed Sep. 1, 2010, 7 pgs.

(56) References Cited

OTHER PUBLICATIONS

U.S. Appl. No. 11/078,399, Preliminary Amendment filed Jan. 7, 2009, 17 pgs.
U.S. Appl. No. 11/078,399, Preliminary Amendment filed Mar. 14, 2006, 1 pg.
U.S. Appl. No. 11/078,399, Response filed Mar. 2, 2010 to Non Final Office Action mailed Dec. 3, 2009, 17 pgs.
U.S. Appl. No. 11/078,399, Response filed Jul. 16, 2009 to Restriction Requirement mailed Jun. 16, 2009, 12 pgs.
U.S. Appl. No. 11/078,399, Response filed Aug. 10, 2010 to Final Office Action maied Jun. 10, 2010, 14 pgs.
U.S. Appl. No. 11/078,399, Restriction Requirement mailed Jun. 16, 2009, 7 pgs.
U.S. Appl. No. 11/780,997, Final Office Action mailed Mar. 2, 2010, 10 pgs.
U.S. Appl. No. 11/780,997, Final Office Action mailed Apr. 8, 2011, 15 pgs.
U.S. Appl. No. 11/780,997, Non-Final Office Action mailed Jun. 5, 2009, 19 pgs.
U.S. Appl. No. 11/780,997, Response filed Apr. 29, 2010 to Final Office Action mailed Mar. 2, 2010, 12 pgs.
U.S. Appl. No. 11/780,997, Response filed Oct. 5, 2009 to Non Final Office Action mailed Jun. 5, 2009, 25 pgs.
U.S. Appl. No. 11/780,997, Response filed Oct. 12, 2010 to Non-Final Office Action mailed Jun. 11, 2010, 15 pgs.
U.S. Appl. No. 11/780,997, Response filed Jun. 8, 2011 to Final Office Action mailed Apr. 8, 2011, 15 pgs.
European Application No. 06795079.0, Office Action Mailed Sep. 25, 2009, 5 pgs.
European Application Serial No. 06795079.0, Response filed May 25, 2010, 12 pgs.
International Application Serial No. PCT/IB2006/001863, International Preliminary Report on Patentability mailed Sep. 18, 2007, 13 pgs.
International Application Serial No. PCT/IB2006/001863, International Search Report and Written Opinion mailed Sep. 18, 2007, 13 pgs.
International Application Serial No. PCT/IB2006/001863, International Search Report mailed May 23, 2007, 5 pgs.
International Application Serial No. PCT/IB2006/001863, Written Opinion mailed Sep. 14, 2007, 12 pgs.
International Application Serial No. PCT/IB2008/001932, International Search Report and Written Opinion dated Mar. 3, 2009, 13 pgs.
International Application Serial No. PCT/US2009/064360, Search Report mailed Mar. 9, 2010, 7 pgs.
International Application Serial No. PCT/US2009/064360, Written Opinion mailed Mar. 9, 2010, 6 pgs.
Graaff, R., "Reduced Light-Scattering Properties for Mixtures of Spherical Particles: A Simple Approximation Derived from Mie Calculations", Applied Optics 31, (1992), 1370-1376.
Keogh, Brian F., "When Pulse Oxinetry Monitoring of the Critically Ill is Not Enough", Anesth Analg 94, (2002), S96-S99.
Page, Andrew J, et al., "Distributed Monte Carlo Simulation of Light Transportation in Tissue", 4 pgs.
Rais-Bahrami, K, et al., "Validation of a noninvasive neonatal optical cerebral oximeter in veno-venous ECMO patients with a cephalad catheter", Journal of Perinatology, (2006), pp. 628-635.
Schmitt, Joseph M., "Simple Photon Diffusion Analysis of the Effects of Multiple Scattering on Pulse Oxinetry", IEEE, vol. 38, No. 12, (Dec. 1991), 1194-1203.
U.S. Appl. No. 12/618,120, Non Final Office Action mailed Jan. 7, 2013, 9 pgs.
U.S. Appl. No. 12/618,120, Response filed Oct. 26, 2012 to Restriction Requirement mailed Jul. 26, 2012, 8 pgs.
European Application Serial No. 06795079.0, Office Action mailed Apr. 11, 2013, 5 pgs.
International Application Serial No. PCT/IB2008/001932, International Preliminary Report on Patentability mailed Feb. 4, 2010, 8 pgs.
Japanese Application Serial No. 2008-501451, Office Action mailed Feb. 8, 2013, with English translation of claims, 7 pgs.
U.S. Appl. No. 12/618,120, Notice of Allowance mailed Sep. 3, 2013, 10 pgs.
U.S. Appl. No. 12/618,120, Response filed Jul. 8, 2013 to Non Final Office Action mailed Jan. 7, 2013, 9 pgs.
Japanese Application Serial No. 2008-501451, Response filed Jul. 8, 2013 to Office Action mailed Feb. 8, 2013, w/English translation, 14 pgs.
U.S. Appl. No. 12/618,120, Notice of Allowance mailed Dec. 24, 2013, 11 pgs.
European Application Serial No. 06795079.0, Summons to Attend Oral Proceedings mailed Dec. 5, 2013, 5 pgs.
European Application Serial No. 06795079.0, Amendment filed Feb. 12, 2014, 20 pgs.
European Application Serial No. 06795079.0, Amendment filed Dec. 7, 2007, 28 pgs.
European Application Serial No. 06795079.0, Office Action mailed Mar. 27, 2014, 25 pgs.
European Application Serial No. 06795079.0, Response filed Aug. 13, 2013 to Office Action mailed Apr. 11, 2013, 11 pgs.
Japanese Application Serial No. 2008-501451, Amendment filed Mar. 9, 2009, w/English claims, 15 pgs.
Japanese Application Serial No. 2008-501451, Amendment filed Apr. 18, 2008, 8 pgs.
Japanese Application Serial No. 2008-501451, Office Action mailed Jan. 24, 2014, English translation, 9 pgs.

* cited by examiner

IN VIVO BLOOD SPECTROMETRY

RELATED APPLICATION

The present application is a continuation of U.S. patent application Ser. No. 11/078,399, filed Mar. 14, 2005, which is incorporated herein by reference in its entirety.

BACKGROUND OF THE INVENTION

1. Field of the Invention

The invention relates to a process and apparatus for increasing the accuracy of optical in vivo measurements of blood constituents in tissue, such as arterial oxygenation.

2. Description of Related Art

A standard method to measure the arterial oxygenation of blood is known as pulse oximetry.

Pulse oximeters function on the basis that at differing wavelengths, blood attenuates light very differently depending upon the level of oxygenation. Pulse waves starting from the heart cause in the arterial blood vessel system a periodic fluctuation in the arterial blood content in the tissue. As a consequence, a periodic change in the light absorption (FIG. 1) can be registered between the light transmitter, whose radiation passes through the tissue, and the receivers, which are integrated in a pulse oximetry sensor. The evaluation of the sensor signals is normally carried out at light wavelengths of w1=660 and w2=940 nm by calculating the differential change of light absorption at times t1 and t2. It is possible to create a measured variable R which is obtained in the following manner or in a similar manner:

$$Rw1, w2 = \frac{\ln(It1, w1) - \ln(It2, w1)}{\ln(It1, w2) - \ln(It2, w2)} \quad (1)$$

The light intensities described in the formula represent the light intensities received in the receiver of the sensors used in pulse oximetry. The measured variable R serves as a measurement for the oxygen saturation. The formation of a quotient in order to form the measured variable is intended to compensate for any possible influences the haemoglobin content of the tissue, the pigmentation of the skin or the pilosity may have on the measurement of the oxygen saturation of arterial blood. The difference of the light attenuations at a minimum and maximum value is the delta of the light attenuations for each of both wavelengths.

Measuring oxygen saturation of arterial blood in the tissue in a range of 70 to 100% using light of wavelength 940 nm and 660 nm most often produces for one single application site sufficiently accurate measured values. However, in order to measure lower oxygen saturation of arterial blood it is necessary to assume a strong influence on the measured variable R in particular caused by perfusion (i.e. blood content) (see: IEEE; Photon Diffusion Analysis of the Effects of Multiple Scattering on Pulse Oximetry by J. M. Schmitt; 1991) and other optical parameters of tissue.

Rall, U.S. Pat. No. 5,529,064, describes a fetal pulse oximetry sensor. For this kind of application, a higher measurement precision is desirable because a fetus has a physiological lower oxygenation than adult human beings and measurement error of $SaO_2$ increases at low oxygenations.

U.S. Pat. No. 6,226,540 to Bernreuter, incorporated by reference herein, improves the precision of pulse oximetry. However, in order to measure on different body sites with the same high resolution for the arterial oxygenation, additional precision to measure optical tissue properties is necessary. Another problem is that pulse oximetry alone does not provide sufficient diagnostic information to monitor critically ill patients (See: When Pulse Oximetry Monitoring of the Critically Ill is Not Enough by Brian F. Keogh in Anesth Analg (2002), 94: 96-99).

Because of this it would be highly desirable to be able to additionally measure the mixed venous oxygenation of blood $SVO_2$. Methods to measure $SvO_2$ with NIR were described by Jobsis in U.S. Pat. No. 4,223,680 and by Hirano et al in U.S. Pat. No. 5,057,695. A problem of those disclosed solutions is that hair, dirt or other optically non-transparent material on the surface of tissue can influence the measured results for $SvO_2$.

To measure the metabolism of blood oxygenation, Anderson et al in U.S. Pat. No. 5,879,294 disclose an instrument in which the second derivative of the light spectrum used delivers information about the oxygenation. Hereby, the influence of light scattering in tissue is minimized, which can result in higher measurement precision. A disadvantage of this solution is that the calibration of the optical instruments is complicated and expensive, which makes it impractical to use such devices for sports activity applications, where light weight wearable devices would be of interest. Similar problems are known for frequency domain spectroscopy disclosed for example in Gratton, U.S. Pat. No. 4,840,485. Oximetry devices, which are described in the present specification and which simply measure light attenuations of tissue at different wavelengths, are more feasible, flexible and reliable in practice than complex time resolved methods.

SUMMARY OF THE INVENTION

Accordingly, several objects and advantages of the invention are:

a) to provide a device that measures the arterial oxygenation of blood in tissue at a certain application site with improved precision;

b) to provide a device that measures the arterial oxygenation blood in tissue at different application sites with improved precision;

c) to provide a device that measures the mixed venous or venous oxygenation blood in tissue with improved precision;

d) to provide a device that measures the mixed venous or venous and arterial oxygenation blood in tissue with improved precision with only one sensor;

e) to provide a device that measures the mixed venous or venous oxygenation blood in tissue with improved precision without complicated empirical calibration;

f) to provide an inexpensive device that measures the mixed venous or venous oxygenation blood in tissue with improved precision;

g) to provide an inexpensive device that can directly measure oxygen extraction of tissue at the application site; and h) to provide an inexpensive, wearable device that measures oxygenation of tissue.

There are various fields of application where the invention can be used with benefit. For example for sports activity applications, a light weight, small and inexpensive device to track the oxygen metabolism would be of interest.

Critically ill persons would benefit by continuous and more detailed diagnostic information of their physiological condition.

Newborns would benefit from better care if arterial oxygenation could be measured e.g. on the back instead on the feet where unintentional alarms more often occur due to motion effects. A higher precision of pulse oximetry could improve ventilation of newborns, and precision of fetal pulse oximetry where a high resolution of the arterial oxygenation is needed, could be improved as well (See U.S. Pat. No. 6,226,540).

In accordance with invention, a device utilizes a combination of light emitters and detectors with:

a light wavelength combination with more than two wavelengths, where the peak spectrum of a third wavelength is about the geometric mean value of the first and second wavelengths;

multiple detectors and emitters which eliminate influences on calibration by subtracting and adding measured light attenuations;

a model-based calibration calculation, which improves precision of measured output variables.

As a result, influences on the calibration of different issue properties can be minimized in order to measure arterial or venous or the combination of arterial and venous oxygenation. It has been discovered that by choosing one of the wavelengths as a geometric mean value of two other wavelengths, variations due to scattering can be reduced. Additional determination of light attenuation can reduce measurement errors because of variations of light absorption due to different tissue composition, i.e., variations of relative amounts of muscle, skin, fat, bone, etc.

It is noted that as used in the present specification, "venous" and "mixed venous" are synonyms, "attenuation" refers to absolute or differential attenuation, "tissue oxygenation" refers to arterial, mixed venous, or venous oxygenation or a combination thereof, and the phrase "about" in reference to wavelengths quantifies in a range of +/−80 nm, and in reference to distance quantifies in a range of +/−2 cm.

DESCRIPTION OF THE PREFERRED EMBODIMENTS

Figure 1:
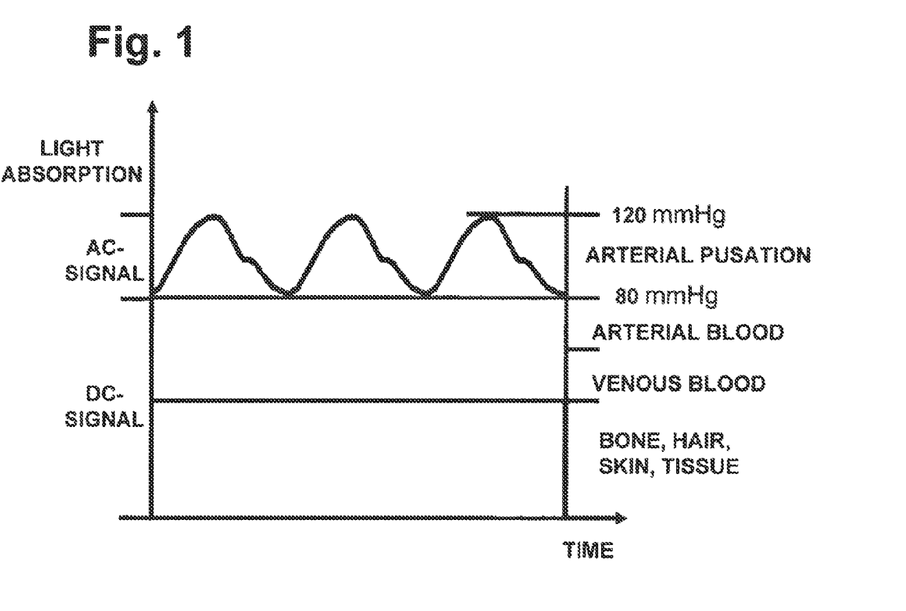
FIG. 1 is a graph showing changes of light absorption by blood over time.

The diagram of FIG. 1 shows the fundamental effect on which pulse oximetry and comparable methods to determine arterial blood oxygenation are based. When measuring light absorption of tissue in vivo light absorption changes synchronously with every heart cycle. The diagram illustrates the change of light absorption versus time, which is caused by arterial pulsations that can be measured while systole and diastole. During systole and diastole the pressure on the arterial vessel system varies from 80 mmHg to 120 mmHg. The change of light absorption is called the AC-signal. The DC-signal, the time-invariant part of light absorption, is caused by the non-pulsating part of the arterial blood, the venous blood, bone, hair, tissue and other constant absorbing constituents versus time. The time-invariant signal is the basis for the calculation of the mixed venous oxygenation of tissue; thus, a major part of the absorption is caused by venous blood and a minor part by arterial blood.

Figure 2:
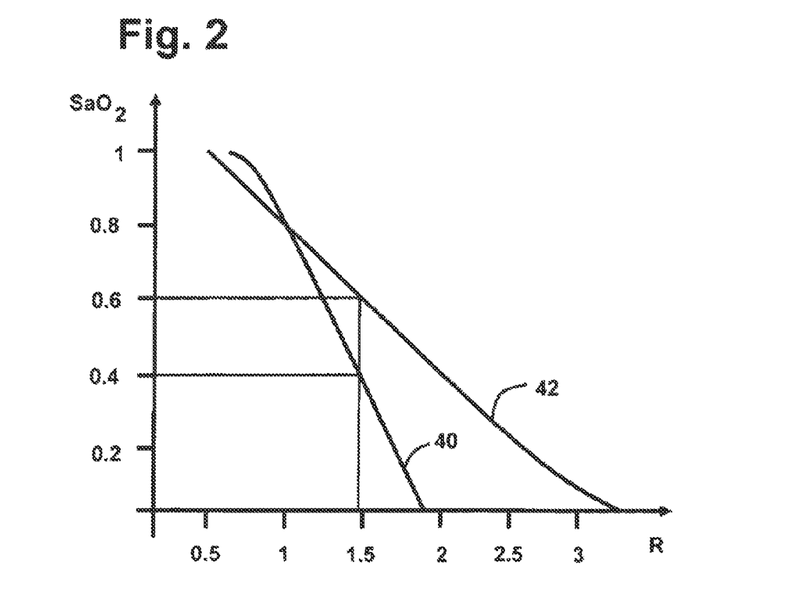
FIG. 2 is a graph illustrating the dependency of arterial oxygen saturation on the measurement variable R for different optical tissue properties.
Figure 6:
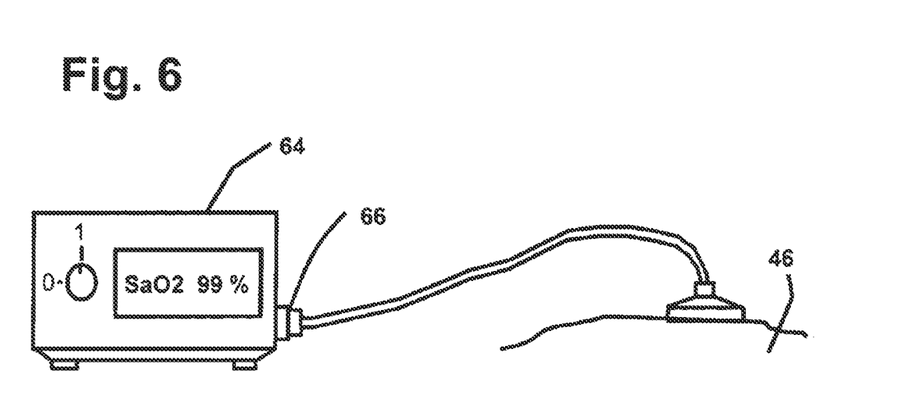
FIG. 6 is a schematic diagram of an oximetry system in operation.
Figure 18:
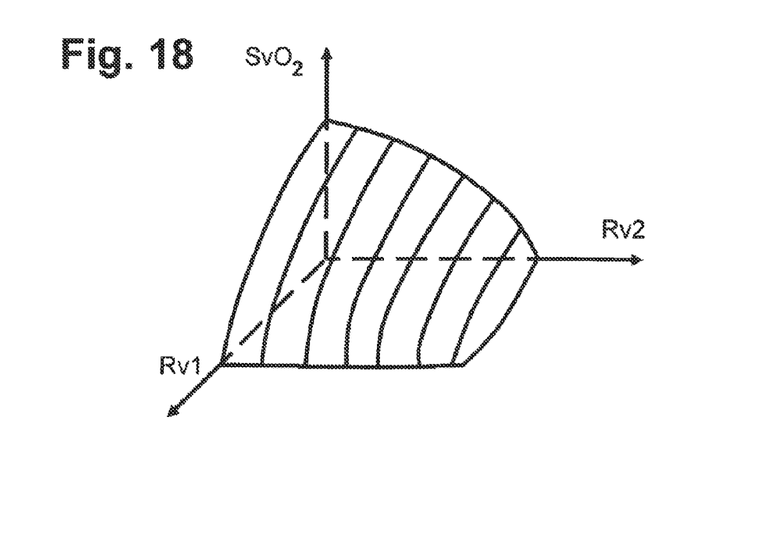
FIG. 18 is a diagram of a multidimensional calibration of oxygenation for the two measuring variables Rv1, Rv2 vs. $SvO_2$.

FIG. 2 shows two calibration curves in a diagram with $SaO_2$ vs. R. Calibration line 42 is only valid for a first distinct set of optical properties. Calibration line 40 is only valid for a second distinct set of optical properties. The valid set of optical properties can be determined by an optical system illustrated in FIGS. 3 and 6 with a sensor 318, which is placed on tissue 46 and connected via a plug 66 to a display device 64. Additionally, FIG. 2 shows two horizontal lines at $SaO_2$=0.6 and at 8a02=0.4 and one vertical line at R=1.4. If an optical system determines only R without registering the two different sets of optical properties, this would result in an error of 0.2 $SaO_2$ ($SaO_2$ at first set of optical properties— $SaO_2$ at second set of optical properties). An analogous relation also exists for the mixed venous saturation of blood $SvO_2$ and a measurement variable Rv1 and Rv2 for mixed venous oxygenation (FIG. 18).

Figure 3:
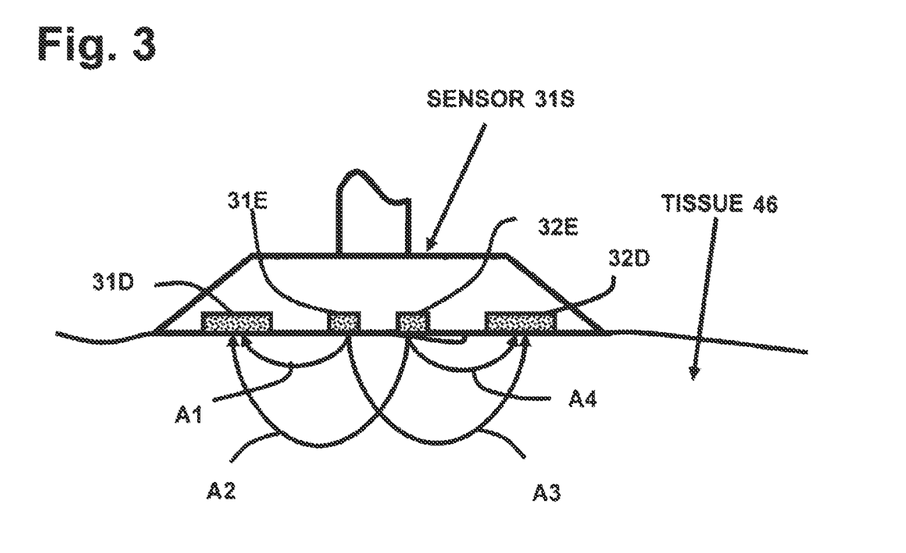
FIG. 3 shows a reflectance oximetry sensor according to the invention in schematic cross-section.

FIG. 3 shows an oximetry sensor 318 on the upper part of the figure which is placed on tissue 46. The sensor 318 contains two light emitters 31E, 32E and two light detectors 310, 320. The arrows A1 through A4 show how light passes from emitters to detectors through tissue. A1 stands representative for light which is emitted in emitter 31E and received in detector 310. A2 is light emitted in emitter 32E and detected in detector 310. A3 is light emitted in 31E and received in 320 and A4 is light emitted in emitter 32E and detected in detector 320.

Figure 4:
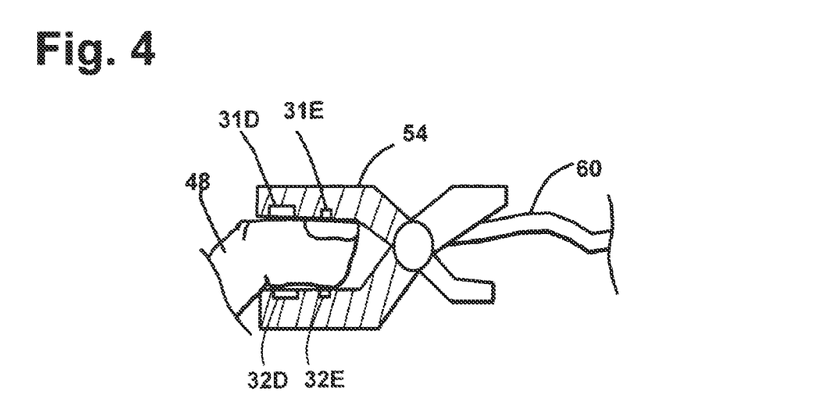
FIG. 4 shows a finger clip sensor according to the invention in schematic cross-section.

FIG. 4 shows a finger clip sensor 54 which is fixed on a finger 48. The finger clip sensor incorporates emitters 31E, 32E and detectors 310, 320. The electrical sensor signals of the finger clip sensor are transmitted via a sensor cable 60. The signals can also be conveniently transmitted wirelessly by means well known in the art (not shown).

Figure 5:
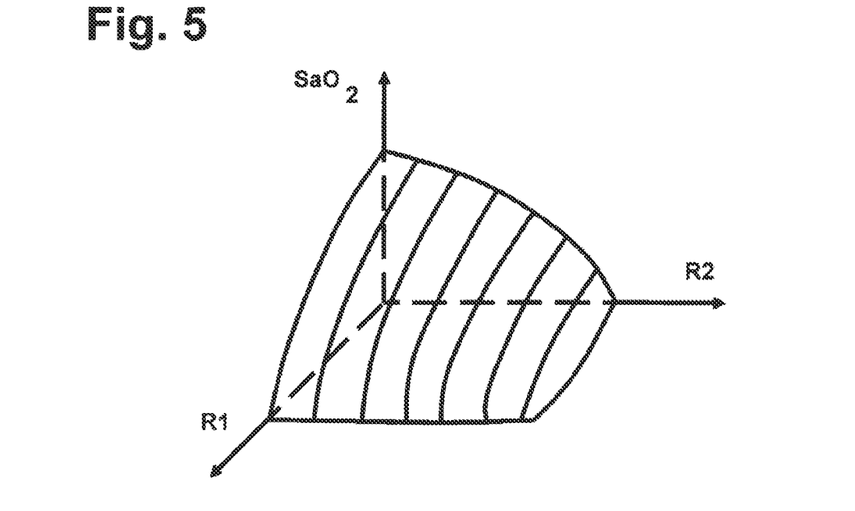
FIG. 5 is a diagram of a multidimensional calibration of oxygenation for the two measuring variables R1, R2 vs. $SaO_2$.

FIG. 5 illustrates a multidimensional calibration of $SaO_2$ vs. R1 and R2. A certain combination of R1 and R2 corresponds to a data point on the calibration plane, which indicates the saturation level $SaO_2$. An analogous relation also exists in FIG. 18 for the mixed venous saturation of blood $SvO_2$ and two related measurement variables Rv1 and Rv2 for mixed venous oxygenation.

Figure 7:
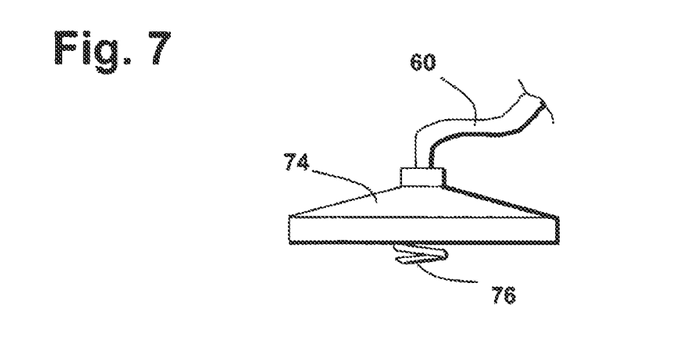
FIG. 7 is a side view of a fetal scalp sensor according to the invention.
Figure 8:
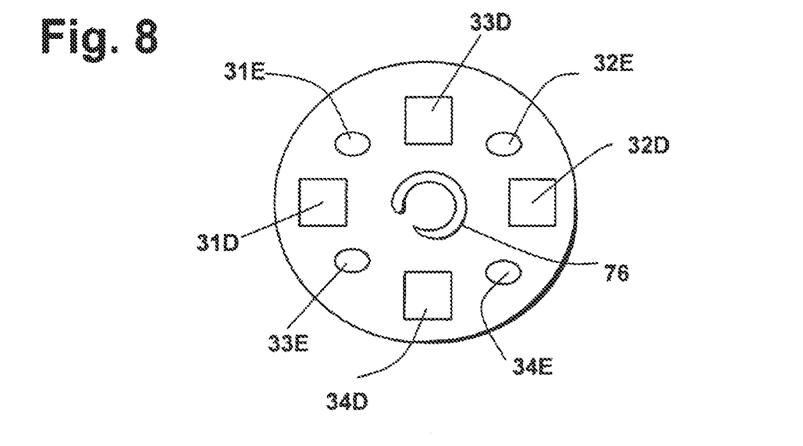
FIG. 8 is a bottom view of the sensor of FIG. 7.

FIGS. 7 and 8 show a fetal scalp sensor 74 with a set of emitters 31E, 32E, 33E and 34E and a set of detectors 310, 320, 330 and 340 from side and bottom views, respectively. The sensor can be fixed on the scalp of the fetus via a spiral needle 76 during labor. Additionally, an electrocardiogramm (ECG) of the fetus can be transmitted via the needle 76.

Figure 9:
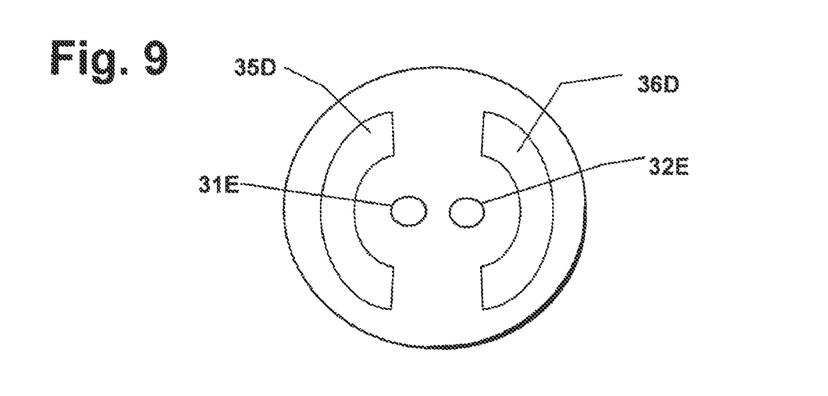
FIG. 9 is a bottom view of the sensor of FIG. 3.

FIG. 9 is a bottom view of sensor 31S from FIG. 3. Detectors 350 and 360 have a concentric form to maximize reception of light emitted by the emitters 31E and 32E.

Figure 10:
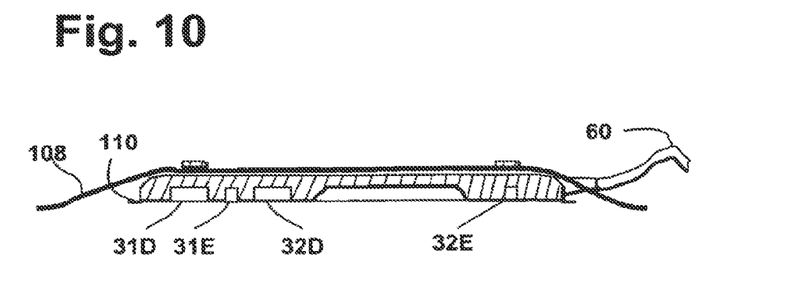
FIG. 10 is a side cross-sectional view of a variation of the sensor of FIG. 3.
Figure 11:
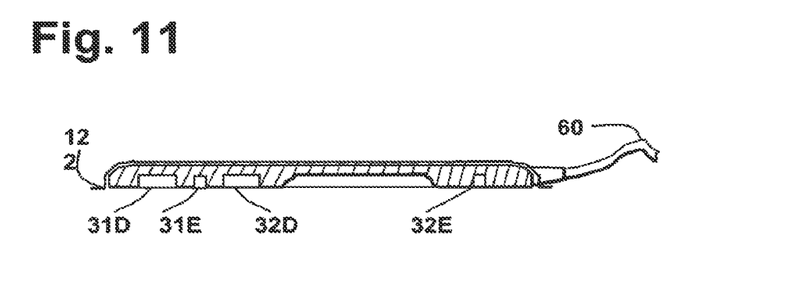
FIG. 11 is a side cross-sectional view of another variation of the sensor of FIG. 3.
Figure 12:
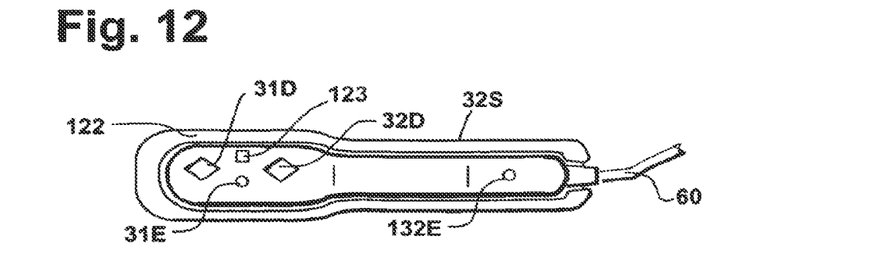
FIG. 12 is a bottom view of the sensor of FIG. 11.

FIGS. 10-12 show several modifications of sensor 31S. FIG. 10 shows sensor in side view with a flat body where detectors 310, 320 and the emitter 320 are grouped close together and emitter 32E is positioned far from this group. The sensor can be fixed via a band 108 on tissue. A light shield 110 minimizes the influence of ambient light.

Figure 13:
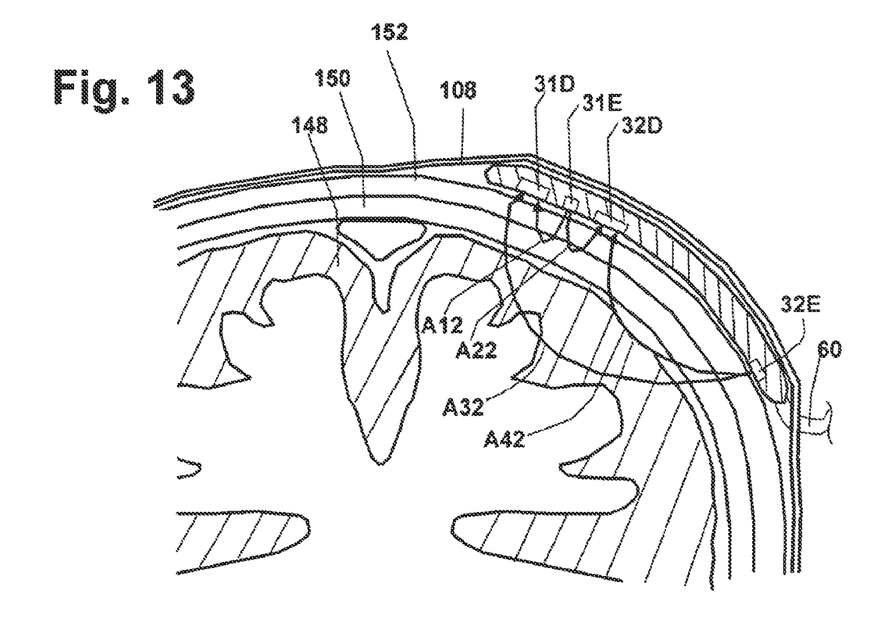
FIGS. 13-14 are side cross-sectional views of reflectance sensors fixed on the forehead.
Figure 14:
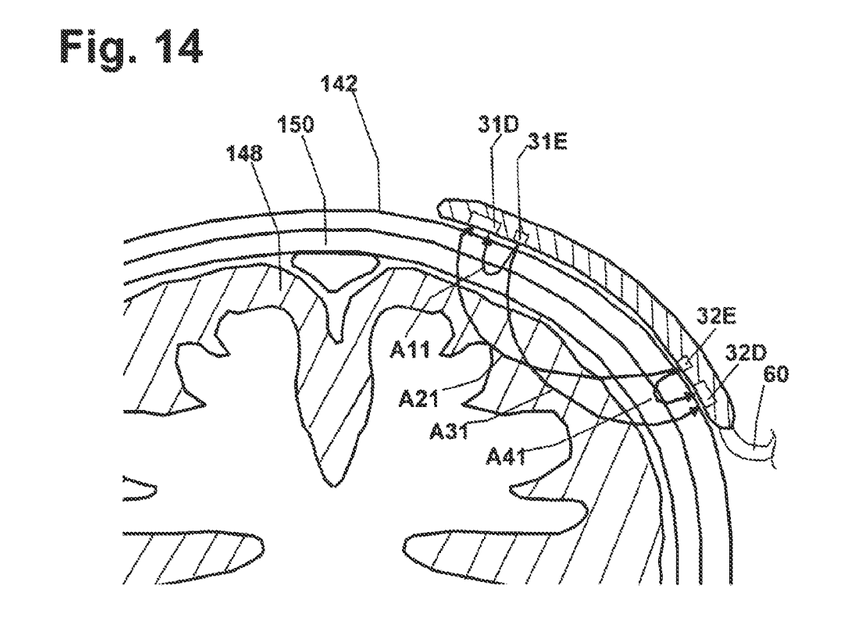

FIG. 11 shows a sensor with a sensor holder 122, while FIG. 12 is a bottom view of sensor of FIG. 11. The bottom side of sensor holder 122 can be covered with medical glue or adhesive. If sensor holder 122 is placed on sensor 31S according to FIG. "11 and applied to tissue 46, fixation is possible by glue on sensor holder 122. Sensor holder 122 can thus be constructed in an inexpensive and disposable manner. Alternatively, the bottom side of the sensor, which is applied to tissue, can be directly covered with glue. The disadvantage of this is that the sensor can not be reused. The heart rate is detected via ECG-electrode 123 which contacts the skin FIGS. 13 and 14 show two variations of sensor 32S applied on the forehead of a person. In the first variation shown in FIG. 13, sensor 32S is fixed via a band 108 to the forehead. The arrows A32 and A42, which represent how light travels from the emitters 31E, 32E to the detectors 31 and 320, pass through forehead tissue 152 and bone of skull 150 and pass or touch brain 148. The arrows A12 and A22 only pass through forehead tissue 152 and bone of skull 150.

The second variation of sensor 32S also applied on the forehead is shown in FIG. 14. The arrows A11, A21, A31 and A41 compared with arrows A12, A22, A32 and A42 of FIG. 13 show that by variation of the position of light detectors and emitters; oxygen content can be sensed differently without changing the outline of the sensor variation used.

Figure 15:
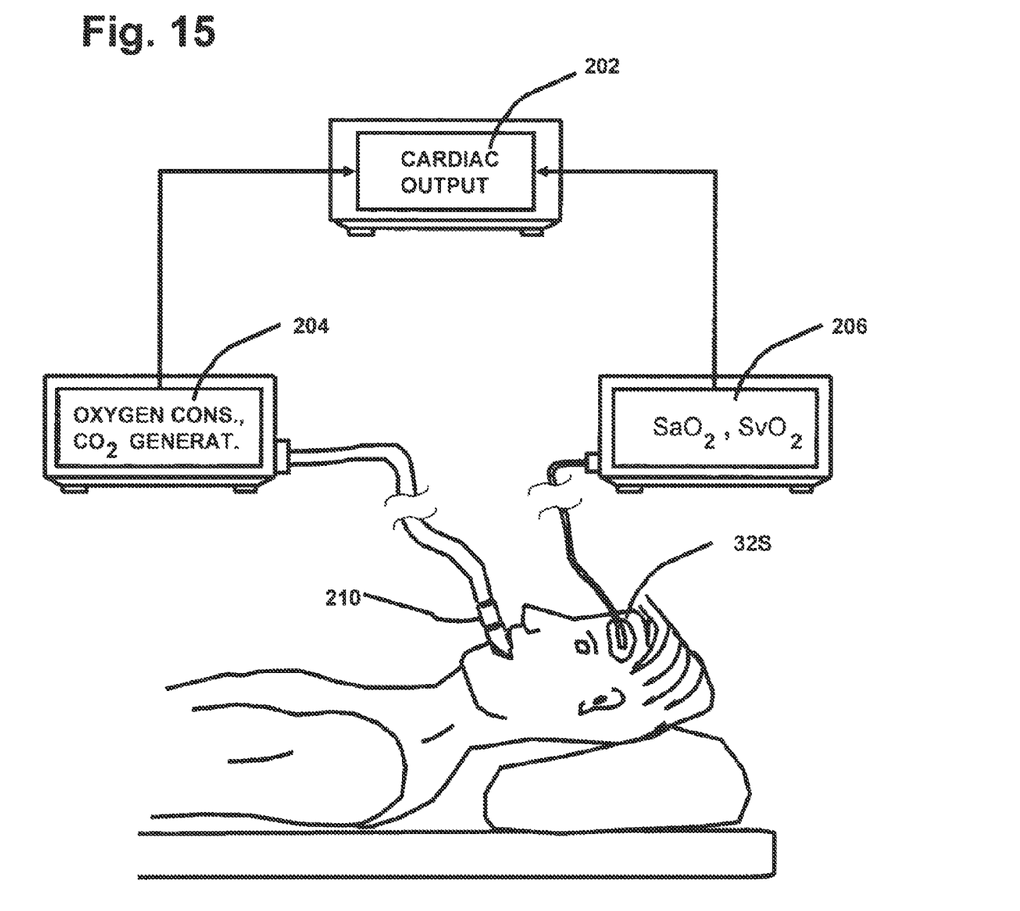
FIG. 15 shows a system for determining cardiac output.

FIG. 15 shows a patient lying on a bed being supplied with oxygen by an intubation tube 210, and an anaesthesia machine 204. The anaesthesic machine 204 is connected to the patient and has an inventive device for measuring oxygen consumption or carbon dioxide production of the patient. The sensor 32S is placed on the forehead of the patient, and is connected with oxygen extraction monitoring device 206, which calculates $SaO_2$ and $SvO_2$ and oxygen extraction. The monitoring device 206 and the anaesthesia machine 204 are linked to a third device 202, which calculates cardiac output or trend of cardiac output.

Figure 16:
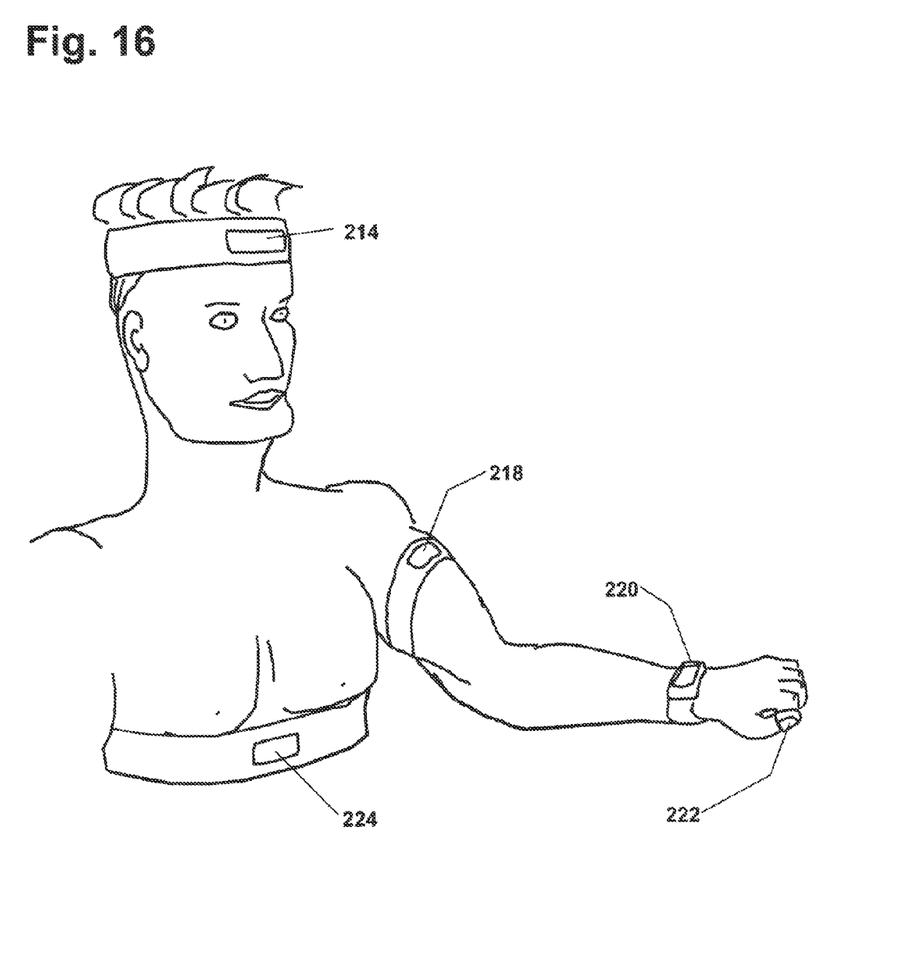
FIG. 16 shows person with wrist worn display and sensor applications on different sites of the body.

FIG. 16 illustrates the use of oxygen monitoring at different application sites for sports activity, in which a wrist worn display device 220 can receive oxygenation data from a forehead-band-sensor 214, from a chest-band-sensor 224, from an arm-band-sensor 218 or from a finger-glove-sensor 222.

Figure 17:
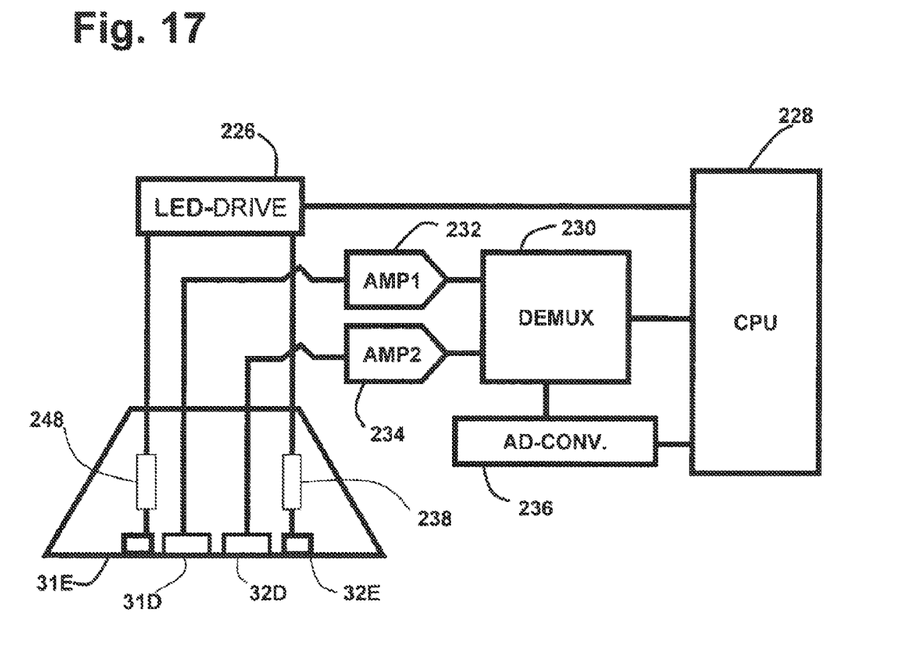
FIG. 17 is a schematic diagram of a hardware processing unit for an oximetry system according to the invention.

FIG. 17 shows the hardware for evaluating oxygenation by using two emitters 31E and 32E and two detectors 31D and 32D. The LED-drive 226 energizes the two emitters via lines 238, 248 which can incorporate coding hardware, to adjust calibration for the multidimensional calibration or to adjust calibration for varying emitter detector geometry. The amplifiers AMP1 232 and AMP2 234 are connected to detectors 31D and 32D. The demultiplexer DEMUX 320 selects each wavelength used in every emitter timed synchronously according to the switching state of the LED-DRIVE 226 and delivers the measured data via an AD-Converter AD-CONV. 236 to the CPU 228.

Figure 19:
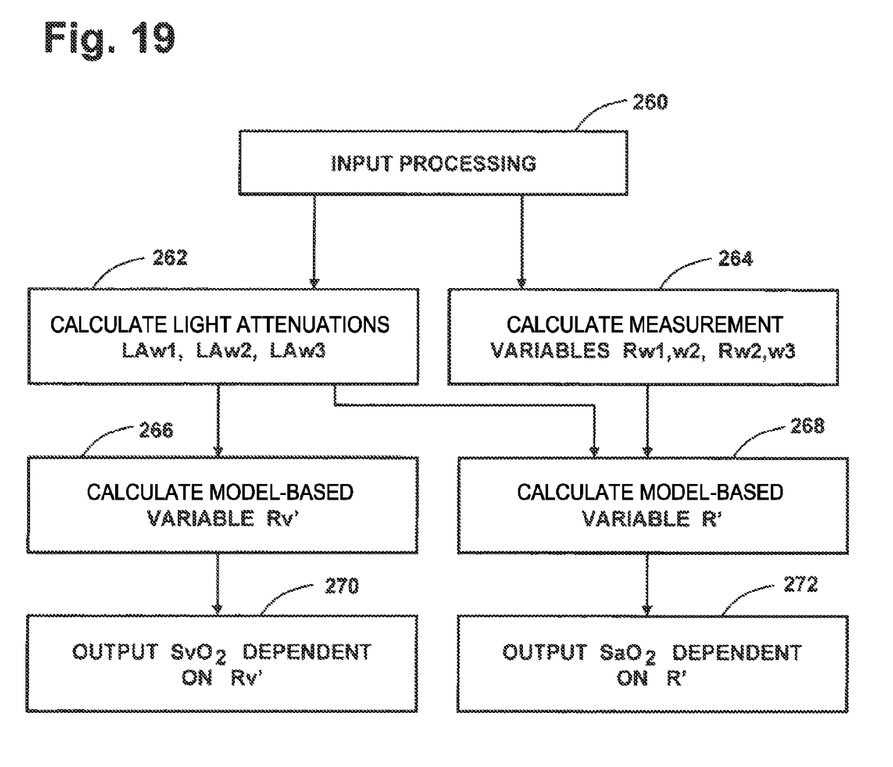
FIG. 19 is a flow chart illustrating signal processing flow for a model-based determination of oxygen in blood.

FIG. 19 illustrates the signal flow of a model-based calibration. An input processing circuit 260 is the first part of the signal flow. The processing circuit is connected with a circuit for calculating light attenuations 262 and a circuit calculating different measurement variables 264. The calculation for light attenuations 262 is a basis for a model-based determination circuit for mixed venous oxygenation 266 with a joint circuit to output a value for the mixed venous oxygenation $SvO_2$ 270. A model-based determination circuit for 20 arterial oxygenation 268 is connected to the circuit for calculating light attenuations 262 and the circuit calculating different measurement variables 264. The output value for a arterial oxygenation circuit for $SaO_2$ 272 is linked to the model-based calculation for $SaO_2$ 268.

By using three instead of two wavelengths to measure the arterial oxygenation, the following approximation can be derived with the help of diffusion theory. The result of this operation is:

$$R' = \frac{Rw2, w1}{Rw1, w0} * \frac{LAw2 * LAw0}{LAw1 * LAw1} + Q \qquad (2)$$

where Rw2, w1 and Rw1,w0 are calculated according to equation (1) using wavelengths w0, w1, and w2 and Q is a correction parameter.

Light attenuation LAwx can be calculated in the following or similar manner:

$$Lawx = \ln(Iwx/Iwxo) \qquad (3)$$

LAwx corresponds to the logarithm of the ratio of light intensity Iwxo which is the emitted and light intensity Iwx the received light passing through tissue at wavelength wx. The index following suffix wx indicates the selected wavelength. Graaff et al showed that scattering in tissue decreases for higher wavelengths according to exponential functions (see: Applied Optics; Reduced Light-Scattering Properties for Mixtures of Spherical Particles: A Simple Approximation Derived from Mie Calculations by R. Graaffi; 1992). Absorption variation may also be taken from other measures or approximations such as the ac/dc ratio. The amplitude may be any measure such as peak-to-peak, RMS, average, or cross correlation coefficient. It may also be derived from other techniques such as Kalman filtering or a measure of the time derivative of the signal. Also, while calculations utilizing ratios of absorptions at different wavelengths are shown, alternate calculations may be used to give the same or approximately the same results. For instance the absorptions could be used directly, without calculating the ratios.

A preferred selection of the wavelengths combination to reduce the influence of scattering is defined by the following equation, with wavelength w1 as the geometrical mean value of wavelength w0 and wavelength w2, defined as:

$$w1 = \sqrt{(w0*w2)} \qquad (4)$$

This combination minimizes the variation band of correction parameter Q, which has a default value of about one. The measurement variable R' of equation (2) has minimized error related to variation of scattering and blood content of tissue.

EXAMPLES

Example 1

The sensor 31S shown in FIG. 3 is used to determine the arterial oxygenation and the mixed venous blood oxygenation of tissue with improved precision. Equation (2) is used to provide a measurement variable R' for the arterial oxygenation. For each of the emitters 31E and 32E, three wavelengths are defined. Initially, two measurement wavelengths w0=940 nm and w2=660 nm are selected. Using equation (4) the third wavelengths w1 is about 788 nm. Wavelength w1 805 nm is chosen because it is close to the calculated third wavelength and is additionally at an isobestic point of the blood absorption spectrum. The next step is to determine the resulting light attenuation LA for each of the three wavelengths w0, w1 and w3:

$$Law1 = LA(A3w1) + LA(A2w1) - LA(A1w1) - LA(A4w1) \quad (5)$$

$$LAw2 = LA(A3w2) + LA(A2w2) - LA(A1w2) - LA(A4w2) \quad (6)$$

$$LAw3 = LA(A3w3) + LA(A2w3) - LA(A1w3) - LA(A4w3) \quad (7)$$

where LA (Axwy) is the logarithm of received light intensity in the detector related to light arrow Ax at wavelength wy. Each LA (Axwy) here is weighted with the factor 1. The suffix x for light arrows Ax represents the number of the selected light arrow and y the suffix for the selected wavelength. Instead of the logarithm of light intensities, light intensity itself can be used in (5)-(7) and "+" is replaced by "*" and "−" is replaced by "/".

In the next step, Rw2, w1 and Rw1, w0 are calculated according to equation (1). As a result R' can be determined using equation (2) with Q as a correction factor which can be dependant on Rw2, w1 or Rw1, w0. The measured arterial oxygenation which is dependant on R' has minimized influence of scattering, blood content or other optical absorbing constituents in tissue.

The quotient in (8) which is part of (2) delivers a measurement variable Rv':

$$Rv' = \frac{LAw2 * LAw0}{LAw1 * LAw1} \quad (8)$$

Rv' is a measure of optical absorption of tissue with decreased influence of scattering. Therefore it can be used as a signal for mixed venous oxygenation $SvO_2$ A mathematically identical form of (2) is:

$$R' = Rw2, w0 * \frac{Rv'}{Rw1, w0 * Rw1, w0} + Q \quad (9)$$

According to (9) the following equation can also be used to determine a measurement variable R1' for $SaO_2$:

$$R1' = Rw2, w0 * f\left(\frac{1}{Rw1, w0 * Rw1, w0}, Rv', Q\right) \quad (10)$$

where f is an empirical function of optical tissue parameters with variables defined above.

An empirical calibration which reduces influence of absorption and scattering of tissue on the measured variables with the variables LAw1, LAw2, LAw3, Rw1, w2 and Rw2, w3 for the whole saturation range of blood is complex. An pure empirical calibration based on these parameters additionally for different application sites is probably impossible. The proposed model-based method reduces complexity of calibration $SaO_2$ can be determined with improved accuracy being only dependent on R'.

It is also possible to use this method for other light absorbing or scattering constituents of blood like carboxyhemoglobin, methemoglobin, bilirubin or glucose dissolved in blood. Light wavelength in the range from 600 nm-1000 nm can be used for carboxyhemoglobin and methemoglobin. Glucose shows an absorption peek dissolved in blood at 1100 nm and bilirubin in the lower wavelengths range from 300 nm-800 nm. For every additional constituent an additional wavelengths has to be chosen. That means that to measure $SaO_2$ and methemoglobin at a time, four wavelength have to be selected and two different measurement variables R'1 and R'2 according equation (9) have to be defined. Accordingly, the resulting output for $SaO_2$ is dependent on R'1 and methemoglobin on R'2.

As a result sensor 31S is able to measure arterial and mixed venous oxygenation and other blood constituents at a time with reduced influence of measurement errors due to scattering and absorption of tissue.

Example 2

In FIG. 4 finger clip sensor 54 is shown with the two emitters 31E, 32E and the two detectors 31D and 32D. The benefit of the finger clip sensor is that it is easy to apply. Equivalent to sensor 31S in FIG. 3, four representative light paths between two emitters and the two detectors are possible so that all calculations according example 1 can be performed in order to calculate the output variables R' and Rv' as a measure for mixed venous and arterial oxygenation in the finger 48. The corresponding calculations can also be performed using sensor of FIG. 9. The difference here is the alternative form of detectors 35D and 36D, which are able to increase detected light intensity due to an enlarged, concentric detector area.

Example 3

FIG. 5 shows a multidimensional calibration of $SaO_2$ vs. R1 and R2. R1 and R2 can be calculated according (1) by selecting two wavelengths pairs where for the first wavelengths pair the wavelengths wm1=660 nm and wm2=910 nm is chosen and for the second wavelengths pair wm3=810 nm and wm2=910 nm. The second wavelengths pair is less sensitive towards arterial oxygenation and is used to compensate errors due to optical tissue parameter variations. In order to guarantee that the multidimensional calibration delivers improved precision in presence of varying tissue parameters, it is important to select exactly the correspondent calibration which is specified for a distinct wavelengths set and a distinct detector emitter distance. Therefore additional information has to be coded to the selected sensor. The tissue oximeter device can read out this information and use the appropriate calibration. The coding of information can be achieved for example by a resistor implemented in the LED drive line of the sensor (see FIG. 17: 248, 238).

A variant of a multidimensional calibration (FIG. 5) can be achieved by calculating R1 according to equation (2) and R2 according to equation (8). This minimizes the error of displayed arterial oxygenation SaO2 due to varying optical tissue absorption.

Example 4

In FIG. 7 a fetal pulse oximetry sensor 74 is shown, which punctures the skin on the head of the fetus with a spiral needle 76. The bottom view of FIG. 8 shows sensor 74 with 4 emitters 31E, 32E, 33E, 34E and four detectors 31D, 32D, 33D, 34D. Apparently, more than four different light paths per selected wavelength between emitters and detectors are possible. This additional information is used to calculate a whole set of resulting light attenuations LAx. For the different light paths it is also possible to compute a set of measurement variables Rx. Generating a mean weighted value (weight can depend on the noise of the related measurement signals) LAm and Rm of the variables LAx and Rx helps to reduce errors due to tissue inhomogeneities. To achieve a stable measure for the optical tissue parameters, which are not influenced by locally varying tissue compositions, is important to minimize errors to precisely determine the inputs of model-based parameters.

Example 5

A brain oximeter is shown in FIG. 13 which is positioned on the right side of the forehead of a patient. The cross section of the brain illustrates how four light paths travel through tissue from emitters 31E, 32E to the detectors 31D and 32D, representative for one wavelength. A resulting light attenuation LA can be achieved for each wavelength by adding light attenuations of A32 and A22 and subtracting therefrom the light attentions which are related to A42 and A12. The resulting light attenuation LA is then independent on dirt on emitters or detectors or on degeneration of those parts, which is an important feature since those sensors can be reused. Three wavelengths are chosen for each of the two emitters 31E and 32E of the sensor in FIG. 13 of the brain oxymeter: wb1=660 nm, wb2=740 nm and wb3=810 nm.

The ratio Rvb of the resulting light attentions LAwb2 and LAwb3 is used as a measure for the mixed venous oxygenation. The resulting light attenuation at wavelength wb3=810 nm can be used to eliminate the dependency of blood content in tissue of Rvb with a multidimensional calibration of $SvO_2$ vs. Rvb and LAwb3.

A preferred emitter-detector distance between emitter 32E and detector 31D is greater than 2 cm. The longer the emitter-detector distance is, the deeper the penetration depth into the brain. In order to achieve maximum penetration depth at a minimum of sensor outline, the distance between an emitter and a detector should be the maximum distance between all emitters and detectors.

FIG. 14 shows an example where within the sensor, the two detectors have the maximum distance and the detector and emitter elements are grouped symmetrically with regard to the center of the sensor. The resulting maximum penetration depth of light path A31, A21 is here less than maximum penetration depth of light path A32 of the sensor which illustrated in FIG. 13 because the maximum emitter detector distance is also less compared to sensor in FIG. 13 at the same total outline of the sensors. Positioning emitters and detectors asymmetrically is therefore the best choice to achieve oxygenation measurements in deep layers of tissue.

Figure 12A:
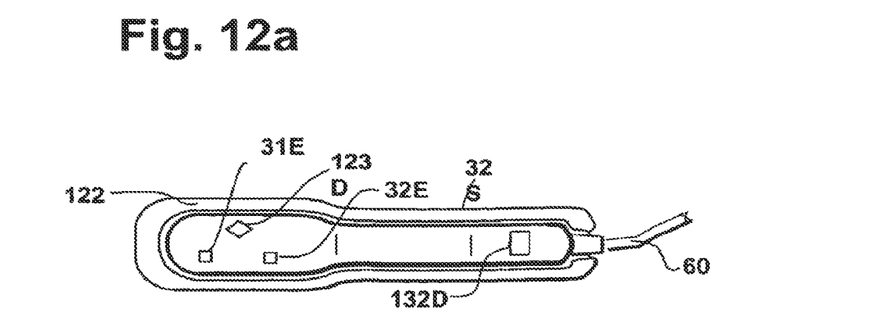
FIG. 12a is a bottom view of a sensor.

FIG. 12 shows a bottom view of a brain oximetry sensor, in which emitter 31E and detectors 31D and 32D are positioned in a triangle. The light paths between emitter 31E and 31D and between 31E and 32D using the wavelengths wb1=660 nm and wb3=810 nm are determined to evaluate the measurement variables Rp1 and Rp2 which are calculated according to equation (1). The mean value of Rp1 and Rp2 is used as the output value for the arterial oxygenation $SaO_2$. Alternatively, as shown in FIG. 12A, the emitters 31E and 32E can be positioned where detectors 31D and 32D are located and detectors 31D and 32D are placed at the location of emitter 31E and 32E in FIG. 12.

Example 6

Referring to Example 5, a brain oximetry sensor was described which is able to determine arterial and mixed venous oxygenation of tissue. These two parameters can be used to calculate the oxygen extraction of tissue. A measure therefor can be the difference of arterial and mixed venous oxygenation. Oxygen extraction reflects how well tissue is supplied with oxygen, and can additionally be used to calculate the cardiac output or the trend of the cardiac output CaOut non-invasively.

FIG. 15 shows a patient being supplied with air via an intubation tube 210. The oxygen consumption or $CO_2$ generation is determined within an anaesthesia machine 204. Brain oximetry sensor 32S is connected to $SaO_2$ and $SvO_2$ display device 206. The information of device 204 and device 206 is evaluated in a cardiac output monitor 202 in the following or similar manner:

$$CaOut = \frac{(\text{oxygen consumption per time})}{SaO_2 SvO_2} \quad (11)$$

Example 7

Knowledge of oxygenation of tissue of parts of the body is of high interest for sports activity monitoring. The oxygenation of the muscles of the upper leg or upper arm can reflect the training level for different activities of sport. FIG. 16 shows an athlete wearing various sensors which are connected by a line or wirelessly with a wrist-worn-display 220. A sports activity sensor can have the same topology as the above mentioned brain sensor of FIG. 12. Emitter-detector distances however vary, depending on desired tissue monitoring depth. Preferred wavelengths to monitor the mixed venous oxygenation are ws1=700 nm, ws2=805 nm and ws3=870 nm. A resulting light attenuation LA is calculated for each wavelength: LWws1, LAws2 and LAws3 with ws1, ws2 and ws3 as index for the selected wavelengths. A measurement variable for the mixed venous oxygenation Rvs is obtained in the following or similar manner:

$$Rvs = \frac{LAws1 - LAws2}{LAws2 - LAws3} \quad (12)$$

Less influence of light scattering and absorption of tissue can be achieved for the determination of mixed venous oxygenation in this way.

A further improvement for better measurement precision can be achieved by generating an output value for the mixed venous oxygenation which is dependant on a multidimensional calibration of $SvO_2$ vs. Rvs and Rv.

Although the description above contains many specificities, these should not be constructed as limiting the scope of the invention but as merely providing illustrations of some of the presently preferred embodiments of this invention. For example the shape of the emitters can be rectangular, emitters can include LEDs, detectors photodiodes; the shape of the brain sensor can be round; the proposed methods to calculate arterial and mixed venous oxygenation of tissue can be combined in different combinations, signals can be processed by Kalman filters in order to reduce influence of noise caused by motion or other unwanted sources, etc.

What is claimed is:

1. A method of determining tissue oxygenation comprising:
   emitting light through the tissue using an emitter, the emitter configured to emit light having at least three wavelengths w1, w2, w3 with a defined relation of wavelengths;
   using a detector to determine at least three light attenuations LAw1, LAw2 and LAw3 for light passing through the tissue, where each light attenuation LAwj corresponds to non-pulsating light intensity received at wj; and
   determining tissue oxygenation based on a model, the model including decreasing scattering influence as a function of wavelength and the model configured to reduce error arising from varying optical properties of the tissue, and wherein tissue oxygenation corresponds to oxygenation of venous blood in tissue.

2. The method of claim 1 wherein wavelength w2 corresponds to the geometrical mean value of wavelength w1 and wavelength w3.

3. The method of claim 1 wherein the model corresponds to an exponential decrease of scattering.

4. An apparatus for determining oxygenation comprising:
   a sensor interface including at least two emitters configured to emit light into a tissue, the emitted light having at least three wavelengths, and including at least two detectors to receive light scattered by the tissue, wherein an emitter-detector distance is selected to provide a depth of penetration of a light path that travels in a selected region of the tissue;
   an information encoder coupled to the sensor interface and configured to provide information about the sensor interface; and
   a processor configured to calculate oxygenation of blood using an output signal from the at least two detectors and using a model and the information from the information encoder, the output signal corresponding to non-pulsating light scattered by the tissue and wherein the output signal corresponds to oxygenation of venous blood in the selected region, the model including decreasing scattering influence as a function of wavelength and the model configured to reduce error arising from varying optical properties of the tissue.

5. The apparatus of claim 4 wherein the information encoder corresponds to variation of an emitted wavelength.

6. The apparatus of claim 4 wherein the information encoder corresponds to a variation of emitter detector geometry.

7. The apparatus of claim 4 configured to select a calibration based on the encoded information.

8. The apparatus of claim 4 wherein the model corresponds to an exponential decrease of scattering.

9. The apparatus of claim 4 wherein the sensor interface is configured as a brain oximetry sensor.

10. An apparatus for measuring oxygenation comprising:
    a sensor interface including at least one light emitter and configured to emit light having at least three different wavelengths into tissue and including at least one detector configured to detect intensity of scattered light through the tissue, the sensor interface configured for coupling to at least one tissue site of a body and having an output corresponding to the intensity, and wherein a selected emitter and a selected detector correspond to a path through a selected region of the tissue; and
    a processor coupled to the output and configured to determine oxygenation using a non-pulsating part of the light and using a model, the model including decreasing scattering influence as a function of wavelength and the model configured to reduce error arising from varying optical properties of the tissue, and wherein the oxygenation corresponds to venous blood of the selected region.

11. The apparatus of claim 10 wherein the model includes exponential decrease of scattering.

12. The apparatus of claim 10 wherein the processor is configured to determine the oxygenation using calibration dependent on at least one light attenuation for at least two body sites, with at least one of the at least two body sites including a forehead, a back, or a chest.

13. The apparatus of claim 10 wherein the sensor interface is configured as a brain oximetry sensor.

14. An apparatus for measuring oxygenation comprising:
    a sensor interface including a light emitter configured to emit light having at least three different wavelengths into tissue and including a detector configured to detect intensity of scattered light through the tissue, the sensor interface configured for coupling to a body site, the sensor interface having an emitter-detector distance selected to provide a depth of penetration of a light path that travels in a selected region of the tissue; and
    a processor configured to determine oxygenation using a non-pulsating part of the light intensity and using a model-based algorithm, the algorithm including decreasing scattering influence with wavelength and configured to reduce error with varying optical properties of the tissue, the oxygenation corresponding to oxygenation of venous blood in the tissue.

15. The apparatus of claim 14 wherein the sensor interface includes two light emitters and detectors and wherein the processor is configured to determine a weight for at least one of light attenuation $LA(A1,wsj)$, light attenuation $LA(A2,wsj)$, light attenuation $LA(A3,wsj)$, and light attenuation $LA(A4,wsj)$ and configured to generate an output determined by adding and subtracting the weighted light attenuations.

16. The apparatus of claim 14 wherein the processor is configured to reduce an influence of an optical tissue property corresponding to an exponential decrease with wavelength.

17. The apparatus of claim 14 further including a memory coupled to the processor, the memory configured store a multidimensional calibration for blood oxygenation.

18. The apparatus of claim 14 wherein the processor is configured to receive an input including attenuations corresponding to LAw1 and LAw2 and is configured to calculate at least one of LAw1/LAw2 or LAw1-LAw2.

19. The apparatus of claim 14 further including means for fixing the sensor interface at the body site, the means for fixing including a band, a sensor holder, a medical glue, or a glove.

20. The apparatus of claim 14 wherein the processor is configured to determine at least one of carboxyhemoglobin, methemoglobin, glucose in blood, Hb, $SvO_2$, $SaO_2$, or bilirubin.

21. The apparatus of claim 14 wherein the sensor interface is configured as a brain oximetry sensor.

22. An apparatus for measuring oxygenation in vivo comprising:
    a sensor interface configured for coupling to a tissue site of a person and including at least one light emitter with at least three different wavelengths, the sensor interface configured to emit light into tissue, and having at least one detector configured to detect light intensity of scattered light;

a processor coupled to the sensor interface and configured for calculating at least three light attenuations LAwsj dependent on the detected light at selected wavelength wsj;

means for fixing the sensor interface at the tissue site, the means for fixing including a band, a sensor holder, a medical glue, a finger glove, or a finger clip;

wherein the processor is configured to implement a model-based algorithm, the algorithm including decreasing scattering influence as a function of an exponential with wavelength and configured to reduce error with varying optical properties of the tissue and configured to generate an output for tissue oxygenation of venous blood in the tissue and based on a non-pulsating part of the at least three light attenuations; and a display coupled to the processor and configured to display the output, the display configured to be worn on a wrist of the person.

23. The apparatus of claim 22 further including a battery coupled to the display.

24. The apparatus of claim 22 wherein the processor is configured to determine pulse rate.

25. The apparatus of claim 22 wherein the sensor interface includes two light emitters and detectors.

26. The apparatus of claim 22 wherein the sensor interface is configured as a brain oximetry sensor.

27. An apparatus for measuring oxygenation comprising a sensor interface having a light emitter configured to emit light having at least three different wavelengths into a tissue and having two detectors configured to detect intensity of scattered light, the sensor interface configured for coupling to tissue at a body site, the sensor interface having a first emitter detector distance selected to provide a depth of penetration of a light path that travels in a selected region of the tissue and having a second emitter detector distance, the first emitter detector distance different from the second emitter detector distance, the sensor interface coupled to a processor, the processor configured to determine oxygenation based on a first output from the sensor interface and based on a second output from the sensor interface, the first output having a non-pulsating part corresponding to oxygenation of blood in the tissue whereby the blood includes venous blood and the second output corresponding to oxygenation of arterial blood, the processor configured to execute an algorithm including decreasing scattering influence with wavelength and configured to reduce error based on varying optical properties of the tissue.

28. The apparatus of claim 27 wherein the second emitter detector distance is less than the first emitter detector distance.

29. The apparatus of claim 27 wherein the first emitter detector distance is about 4 cm.

30. The apparatus of claim 27 wherein the algorithm corresponds to exponential decreasing scattering with wavelength.

31. The apparatus of claim 27 wherein the sensor interface is configured as a brain oximetry sensor.

32. An apparatus for measuring oxygenation in vivo comprising:

a sensor interface configured for coupling to a tissue site proximate a wrist of a person and including at least one light emitter with at least three different wavelengths, the sensor interface configured to emit light into tissue, and having at least one detector configured to detect light intensity of scattered light;

a processor coupled to the sensor interface and configured for calculating at least three light attenuations LAwsj dependent on a non-pulsating part of the detected light at selected wavelength wsj, the processor configured to generate an output for tissue oxygenation based on venous blood in the tissue and using the at least three light attenuations, the processor configured to implement a model including decreasing scattering influence with wavelength and the model configured to reduce error with varying optical properties of the tissue; and a band configured for fixing the sensor interface at the wrist and having a display coupled to the output.

33. The apparatus of claim 32 wherein the model corresponds to exponential decreasing scattering with wavelength.

* * * * *